United States Patent [19]

Jensen

[11] 4,011,326
[45] Mar. 8, 1977

[54] 2-SUBSTITUTED OXAZOLO[4,5-b]PYRIDINE ANTI-INFLAMMATORY AGENTS

[75] Inventor: Norman P. Jensen, New Providence, N.J.

[73] Assignee: Merck & Co., Inc., Rahway, N.J.

[22] Filed: July 29, 1975

[21] Appl. No.: 600,169

[52] U.S. Cl. .......................... 424/256; 260/296 H
[51] Int. Cl.$^2$ .................................. C07D 498/04
[58] Field of Search ................ 260/296 H; 424/256

[56] References Cited
UNITED STATES PATENTS 3,935,195  1/1976  Crounse ........................... 260/240

FOREIGN PATENTS OR APPLICATIONS 2,330,109  1/1974  Germany

Primary Examiner—Henry R. Jiles
Assistant Examiner—C. M. S. Jaisle
Attorney, Agent, or Firm—Frank M. Mahon; William H. Nicholson; Harry E. Westlake, Jr.

[57] ABSTRACT

Oxazolo[4,5-b]pyridine substituted in the 2-position with a polyhydrobicycloaryl group are topical anti-inflammatory agents. They are prepared by condensing a 2-amino-3-hydroxypyridine with the appropriate carboxylic compound.

5 Claims, No Drawings

2-SUBSTITUTED OXAZOLO[4,5-b]PYRIDINE ANTI-INFLAMMATORY AGENTS

This invention is concerned with novel 2-substituted oxazolopyridines, their use as medicaments, processes for their preparation, and pharmaceutical compositions comprising the novel compounds.

In particular, this invention is concerned with novel 2-substituted oxazolo [4,5-b]pyridines, processes for their preparation, their use as topical anti-inflammatories and pharmaceutical compositions comprising the novel compounds.

The topical anti-inflammatories of this invention find utility in dermatoses such as sunburn; atopic dermatitis; contact dermatitis; eczema of the hands and feet, including dyshidrosis and pompholyx; nummular eczema; neurodermatitis; lichen simplex chronicus; eczematous dermatitis; lichen planus; infantile eczema; psoriasis; seborrheic dermatitis; otitis externa; stasis dermatitis; insect bites; exfoliative dermatitis; acute actinic dermatitis; cheilitis; eczematoid mycotic dermatitis; food eczema; neurotic excoriations; postanal surgery; pruritus with lichenification; anogenital pruritus; intertrigo; miliaria; and diaper rash. The only anti-inflammatory agents presently employed for the therapeutic treatment of these conditions are the anti-inflammatory steroids and to a small extent phenylbutazone. These are the same anti-inflammatory agents commonly used systemically for the treatment of inflammatory diseases, and whether used systemically or topically, manifest all their well known undesirable side effects.

Surprisingly, it has been found that the novel compounds of this invention are potent anti-inflammatory agents as measured by their ability to inhibit prostaglandin synthetase and yet systemically they have a low order of anti-inflammatory activity as measured by the carrageenin induced rat paw inflammation test, presumably because of rapid metabolism. The novel compounds of this invention are thus essentially devoid of undesirable systemic side effects and yet are potent prophylactic and therapeutic topical anti-inflammatory agents as confirmed by their ability to prevent or cure ultraviolet erythema (sunburn).

The novel compounds of this invention have the following structural formula:

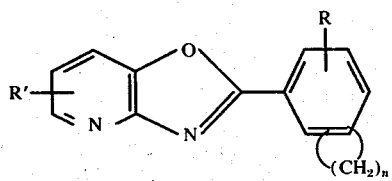

wherein
n is 3–5;
R is
1. hydrogen,
2. halo, such as chloro, bromo or fluoro,
3. lower alkyl, especially $C_{1-5}$ alkyl, or
4. lower alkoxy, especially $C_{1-5}$ alkoxy;
R' is
1. hydrogen, or
2. lower alkyl, especially $C_{1-5}$ alkyl; and
—$(CH_2)n$— is linked to adjacent carbon atoms of the benzo group.

A preferred embodiment of the novel compounds of this invention is the compounds of formula:

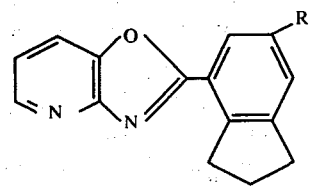

wherein R is lower alkyl.

The compounds of this invention may be prepared by condensation cyclization of an amino-hydroxypyridine with a carboxylic acid, acid anhydride, or acid halide, of formula

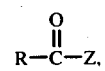

wherein Z is —OH,

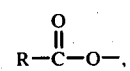

or halide according to the following equation:

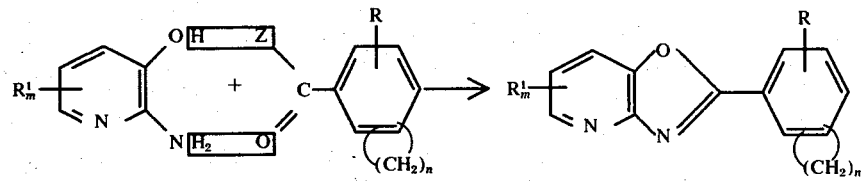

Depending on the condensing agent employed, the reaction can appear as either a concerted one-step ring closure or a two-step process comprising as the first step, the formation of an amide followed by ring closure of the amide to form the oxazolo ring. In many instances it is found advisable and convenient to isolate the intermediate amide and ring close in a second discrete step.

The oxazolopyridines in general can be prepared by condensation of an (amino) hydroxypyridine with an acid anhydride either with or without the influence of a condensing agent such as polyphosphoric acid. In either case the amino hydroxypyridine is mixed with 1 to about 3 molar equivalents of the anhydride and heated to reflux temperature for about 5 to about 30 minutes. After some cooling the excess polyphosphoric acid and anhydride are decomposed and the product is isolated by standard techniques.

The oxazolopyridines can also be prepared by condensation of the appropriate (amino) hydroxypyridine with a carboxylic acid under the influence of polyphosphoric acid. A mixture of the pyridine and a slight excess of a carboxylic acid, in the presence of polyphosphoric acid is heated for about 5 minutes to about 2 hours at a temperature of from 100° to about 300° C., preferably between about 130° and 230° C. The polyphosphoric acid is decomposed with water and the desired product is obtained by making the solution alkaline.

The oxazolopyridines may be prepared via an intermediate amide by reacting an acid halide with the appropriate (amino) hydroxypyridine preferably in approximately equimolar amounts in the presence of an acid acceptor. Any of the common acid acceptors normally employed in N-acylations can be used, but it is found convenient to use an organic base such as pyridine, triethylamine or an equivalent base. Sufficient organic base can be employed to act also as the solvent, or another inert organic solvent such as dimethylformamide, benzene, dioxane, glyme or diglyme or the like, can be used as a medium for the reaction. The amide produced by the above reaction is then ring-closed to an oxazolopyridine by refluxing a mixture of it and a condensing agent such as phosphorus oxychloride for from 1 to about 20 hours, or by heating the amide with polyphosphoric acid at about 100° to about 300° C., preferably at about 130° to about 230° C. for 5 to about 60 minutes. Other condensing agents usable in place of phosphorus oxychloride are phosphorus pentoxide, phosphorus oxybromide, thionyl chloride, and phosphorus tribromide.

In the novel method of treatment of this invention a pharmaceutical composition designed for topical application and comprising a novel compound of this invention is administered directly onto the area of the skin which is inflamed or is exposed to an inflammatory stimulus.

The pharmaceutical compositions of this invention include creams, ointments, gels, solutions, or suspensions commonly employed for topical application and include about 0.01 to 2.0%, preferably about 0.1% by weight of active compound, in admixture with a suitable vehicle.

A typical pharmaceutical composition is prepared as follows: About 2.60 g. of hydroxypropyl cellulose is added to a solution of 0.05 g. of disodium edetate in 13.00 g. purified water while agitating the mixture and maintaining the temperature at about 60° C., and the agitation is continued until the hydroxypropyl cellulose is completely dispersed and wetted. To the resulting dispersed mixture is added, with agitation, a solution containing 0.1 g. of active ingredient dispersed in a mixture of 30.00 g. of anhydrous isopropyl alcohol and 54.25 g. of propylene glycol. The resulting gel mixture is stirred vigorously at room temperature for a period of approximately 15 minutes thereby forming a pharmaceutical composition adapted for the treatment of topical anti-inflammatory conditions.

The following examples describe the chemical sysnthesis of several specific compounds of this invention and the preparation of certain pharmaceutical compositions. They are not intended to limit the scope of the invention to the compounds and formulations but rather to provide adequate directions to permit one skilled in the art to prepare any of the compounds or formulations within the generic scope of the invention and obvious equivalents thereof.

EXAMPLE 1

2-(5,6,7,8-Tetrahydronaphth-1-yl)oxazolo[4,5-b]pyridin

A mixture of 15.5 g. (0.141 mole) of 2-amino-3-hydroxypyridine, 25.0 g. (0.141 mole) of 5,6,7,8-tetrahydronaphthalen-1-carboxylic acid and 75 g. of polyphosphoric acid was placed in oil bath at about 100° C. and heated to 180° C. over a period of 70 minutes. The mixture was poured into 1 l. of ice-water and adjusted to pH 6 with solid sodium bicarbonate and finally to pH 10 with concentrated ammonium hydroxide. Methylene chloride (500 ml.) was added and stirring was continued for 2 hours. The aqueous phase was separated and extracted with 2 × 250 ml. of methylene chloride. The combined extracts were dried over magnesium sulfate, filtered, and concentrated to dryness to give 30.0 g. of product, m.p. 87°–90° C. Recrystallization from 300 ml. of cyclohexane gave 24.2 g. of 2-(5,6,7,8-tetrahydronaphth-1-yl)oxazolo[4,5-b]pyridin, m.p. 88°–91° C.

Employing the procedure substantially as described in Example 1, but substituting for the 5,6,7,8-tetrahydronaphthalene-1-carboxylic used therein a molar equivalent of a carboxylic acid of formula:

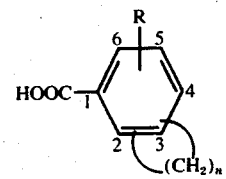

and a pyridine of formula:

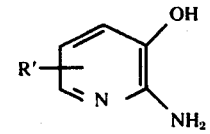

described in Table I, there are produced the 2-substituted oxazolo[4,5-b]pyridines also described in Table I in accordance with Equation I.

Equation I

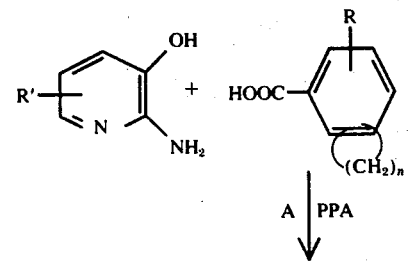

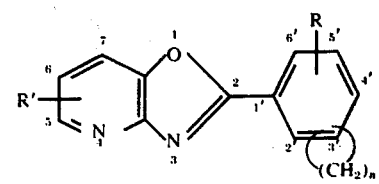

Table I

| R' | R | -(CH$_2$)n- | m.p. |
|---|---|---|---|
| H | H | 3'-(CH$_2$)$_4$-4' | 119–121 |
| H | H | 2'-(CH$_2$)$_3$-3' | 94–96 |
| H | H | 3'-(CH$_2$)$_3$-4' | |
| 5-CH$_3$ | H | 2'-(CH$_2$)$_3$-3' | |
| H | H | 2'-(CH$_2$)$_5$-3' | |
| 5-CH$_3$ | 5'-C(CH$_3$)$_3$ | 2'-(CH$_2$)$_3$-3' | 181–183° |

EXAMPLE 2

2-(3-Chloro-5,6,7,8-tetrahydronaphth-1-yl)oxazolo[4,5-b]-pyridine

Step A: Preparation of 3-nitro-5,6,7,8-tetrahydronaphthalene-1-carboxylic acid

Fuming red nitric acid (150 ml.) was cooled to 2° C. and 27.3 g. of 5,6,7,8-tetrahydronaphthalene-1-carboxylic acid was added portionwise over 0.5 hour with stirring maintaining the temperature at 2°–6° C. After another 45 minutes at about 5° C. the mixture was poured into 1500 ml. of crushed ice. The precipitate was collected and washed well with 5 × 500 ml. portions of water. The dried precipitate was heated with about 200 ml. of benzene. The insoluble material was collected and recrystallized from ethyl acetate to give 3-nitro-5,6,7,8-tetrahydronaphthalene-1-carboxylic acid, m.p. 209°–212° C.

Step B: Preparation of 3-amino-5,6,7,8-tetrahydronaphthalene-1-carboxylic acid

The nitro compound from Step A (2.72 g.) was hydrogenated in 50 ml. of methanol over 200 mg. of 5% palladium on carbon. The catalyst was removed on a filter and the filtrate was evaporated to dryness to give 2.23 g. of 3-amino-5,6,7,8-tetrahydronaphthalene-1-carboxylic acid, m.p. 178°–180° C.

Step C: Preparation of 3-chloro-5,6,7,8-tetrahydronaphthalene-1-carboxylic acid

A slurry of 2.2 g. of the amino compound from Step B in 12 ml. of 6 N hydrochloric acid was cooled to 2° C. and a solution of 0.87 g. of sodium nitrite in 3 ml. of water was added over 15 minutes while keeping the temperature at ≤ 5° C. After another 10 minutes at ~5° C., it was poured into an ice cold solution of 1.50 g. of cuprous chloride in 7 ml. of concentrated hydrochloric acid, and the mixture was stirred 2 hours at about 30° C. The precipitate was collected, washed with water and dried to give 2.3 g. of crude product, m.p. 130°–140° C. This was dissolved in benzene, treated with magnesium sulfate, charcoal and diatomaceous earth, filtered and concentrated to dryness. The residue was recrystallized from 20 ml. of cyclohexane to give 1.04 g. of 3-chloro-5,6,7,8-tetrahydronaphthalene-1-carboxylic acid, m.p. 148°–151.5° C.

Step D: Preparation of 2-(3-chloro-5,6,7,8-tetrahydronaphth-1-yl)oxazolo[4,5-b]pyridine A mixture of 0.98 g. of the product from Step C, 0.55 g. of 2-amino-3-hydroxypyridine, and 13 g. of polyphosphoric acid was heated to 210° C. over 45 minutes, poured onto 200 ml. of ice-water, and stirred 1 hour. The precipitate was collected, washed with water and dilute sodium hydroxide solution and extracted with 20 ml. of hot benzene. The benzene was evaporated to dryness, and the residue was recrystallized from cyclohexane to give 0.68 g. of 2-(3-chloro-5,6,7,8-tetrahydronaphth-1-yl)-oxazolo[4,5-b]pyridine, m.p. 129.5°–131.5° C.

EXAMPLE 3

2-(4-Fluoro-5,6,7,8-tetrahydronaphth-2-yl)-5-methyloxazolo[4,5-b]pyridine

Step A: Preparation of 4-nitro-5,6,7,8-tetrahydronaphthalene-2-carboxylic acid

Employing the procedure substantially as described in Example 2, Step A, but substituting for the 5,6,7,8-tetrahydronaphthalene-1-carboxylic acid used therein, an equimolar amount of 5,6,7,8-tetrahydronaphthalene-2-carboxylic acid, there is produced 4-nitro-5,6,7,8-tetrahydronaphthalene-2-carboxylic acid.

Step B: Preparation of 4-amino-5,6,7,8-tetrahydronaphthalene-2-carboxylic acid

Employing the procedure of Example 2, Step B, but substituting for the 3-nitro-5,6,7,8-tetrahydronaphthalene-1-carboxylic acid used therein, an equimolar amount of 4-nitro-5,6,7,8-tetrahydronaphthalene-2-carboxylic acid, there is produced 4-amino-5,6,7,8-tetrahydronaphthalene-2-carboxylic acid.

Step C: Preparation of 4-fluoro-5,6,7,8-tetrahydronaphthalene-2-carboxylic acid

A mixture of 9.55 g. of 4-amino-5,6,7,8-tetrahydronaphthalene-2-carboxylic acid, 100 ml. of methanol, and 5 ml. of concentrated hydrochloric acid is stirred and refluxed for 15 hours.

The mixture is concentrated in vacuo and the residue taken up in 200 ml. of ether. The ether layer is washed with sodium bicarbonate solution, dried over magnesium sulfate and concentrated to dryness.

The residue is stirred in 25 ml. of concentrated hydrochloric acid, cooled to −2° C. and treated with 0.050 mole of sodium nitrite in 15 ml. of water over a 15 min. period keeping the temperature below 5° C. After 0.5 hour at 0° C., a solution of 0.055 mole of boric acid in 0.2 mole of 60% hydrofluoric acid is added rapidly maintaining the temperature below 7° C. After 0.5 hour at 5° C. the resultant solid is collected on a filter, washed with 15 ml. of cold water, 15 ml. of methanol, and 10 ml. of ether, and dried at room temperature and a pressure of 50 μ. This material is then decomposed in 250-ml. flask by cautious application of a gas flame until a melt is obtained and evolution of fumes ceases. The residue is then extracted with 5 × 20 ml. of chloroform. The chloroform extracts are filtered and concentrated to a residue which is refluxed and stirred with 0.06 mole of potassium hydroxide in 20 ml. water and 10 ml. ethanol for 24 hours. The mixture is concentrated to remove the ethanol, filtered after treating with charcoal, and acidified with dilute hydrochloric acid. The precipitate is collected and recrystallized from cyclohexane to give 4-fluoro-5,6,7,8-tetrahydronaphthalene-2-carboxylic acid.

Step D: Preparation of 2-(4-fluoro-5,6,7,8-tetrahydronaphth-2-yl)-5-methyloxazolo[4,5-b]pyridine Employing the procedure substantially as described in Example 1, but substituting for the 2-amino-3-hydroxypyridine and the 5,6,7,8-tetrahydronaphthalene-1-carboxylic acid used therein, equimolar amounts of 2-amino-3-hydroxy-6-methylpyridine and 4-fluoro-5,6,7,8-tetrahydronaphthalene-2-carboxylic acid respectively, there is produced 2-(4-fluoro-5,6,7,8-tetrahydronaphth-2-yl)-5-methyloxazolo[4,5-b]pyridine.

EXAMPLE 4

5-(1-Methylpropyl)-2-(4-methyl-5,6,7,8-tetrahydronaphth-1-yl)oxazolo[4,5-b]pyridine Step A: Preparation of 2-amino-3-hydroxy-6-(1-methylpropyl)pyridine 6-(1-methylpropyl)-3-hydroxy-2-nitropyridine (23 g.) in 450 ml. of methanol is hydrogenated over 1 gm. of 5% palladium on carbon catalyst for 3 hours. The catalyst is removed on a filter and the filtrate is concentrated to dryness to give 2-amino-3-hydroxy-6-(1-methylpropyl)pyridine.

Step B: Preparation of 5-(1-methylpropyl)-2-(4-methyl-5,6,7,8-tetrahydronaphth-1-yl)oxazolo[4,5-b]pyridine Employing the procedure substantially as described in Example 1, but substituting for the 2-amino-3-hydroxypyridine and 5,6,7,8-tetrahydronaphthalene-1-carboxylic acid used therein, equimolar amounts of 2-amino-3-hydroxy-6-(1-methylpropylpyridine and 4-methyl-5,6,7,8-tetrahydronaphthalene-1-carboxylic acid, respectively, there is obtained 5-(1-methylpropyl)-2-(4-methyl-5,6,7,8-tetrahydronaphth-1-yl)oxazolo[4,5-b]pyridine.

EXAMPLE 5

2-(6-Bromo-indan-4-yl)oxazolo[4,5-b]pyridine

Step A: Preparation of 6-nitroindane-4-carboxylic acid

Employing the procedure substantially as described in Example 2, Step A, but substituting for the 5,6,7,8-tetrahydronaphthalene-1-carboxylic acid used therein, an equimolar amount of indane-4-carboxylic acid, there is produced 6-nitroindane-4-carboxylic acid.

Step B: Preparation of 6-aminoindane-4-carboxylic acid

Employing the procedure substantially as described in Example 2, Step B, but substituting for the 3-nitro-5,6,7,8-tetrahydronaphthalene-1-carboxylic acid used therein, an equimolar amount of 6-nitroindane-4-carboxylic acid, there is produced 6-aminoindane-4-carboxylic acid.

Step C: Preparation of 6-bromoindane-4-carboxylic acid

A mixture of 0.03 mole of 6-aminoindane-4-carboxylic acid and 30 ml. of 6 n hydrochloric acid is stirred and cooled to 0° C. and a solution of 0.03 mole sodium nitrite in 10 ml. of water is added dropwise over a 15 minute period keeping the temperature below 4° C. After 15 minutes at 1° C. an ice-cold solution of 0.04 mole of cuprous bromide in 20 ml. of concentrated hydrochloric acid is added. After stirring 4 hours at room temperature, the precipitate is collected, washed with water, dried and recrystallized from cyclohexane to give 6-bromoindane-4-carboxylic acid.

Step D: Preparation of 2-(6-bromo-indan-4-yl)oxazolo[4,5-b]pyridine

Employing the procedure of Example 1, but substituting for the 5,6,7,8-tetrahydronaphthalene-1-carboxylic acid used therein an equimolar amount of 6-bromoindane-4-carboxylic acid, there is produced 2-(6-bromo-indan-4-yl)oxazolo[4,5-b]pyridine.

EXAMPLE 6

5-Ethyl-2-(3-methoxy-5,6,7,8-tetrahydronaphth-1-yl)oxazolo[4,5-b]pyridine

Step A: Preparation of 3-hydroxy-5,6,7,8-tetrahydronaphthalene-1-carboxylic acid 3-Amino-5,6,7,8-tetrahydronaphthalene-1-carboxylic (0.02 mole) in 1300 ml. of 14% sulfuric acid is stirred and heated to reflux and a solution of 0.022 mole of sodium nitrite in 200 ml. of water is added dropwise over a period of 15 minutes. The mixture is cooled and extracted with 10 × 250 ml. of methylene chloride. The extracts are combined, dried over magnesium sulfate, and concentrated in vacuo to give crude 3-hydroxy-5,6,7,8-tetrahydronaphthalene-1-carboxylic acid.

Step B: Preparation of 3-methoxy-5,6,7,8-tetrahydronaphthalene-1-carboxylic acid A mixture of 0.02 mole of 3-hydroxy-5,6,7,8-tetrahydronaphthalene-1-carboxylic acid, and 40 ml. of 2 N sodium hydroxide solution is treated with 0.04 mole of dimethylsulfate over a 5 minutes period, and the mixture is stirred for 24 hours. The mixture is washed with 3 × 50 ml. of ether and acidified with dilute hydrochloric acid. The precipitate is collected, washed with water, dried at room temperature and 100$\mu$ pressure and recrystallized from cyclohexane.

Step C: Preparation of 5-ethyl-2-(3-methoxy-5,6,7,8-tetrahydronaphth-1-yl)oxazolo[4,5-b]pyridine Employing the procedure of Example 1, but substituting for the 5,6,7,8-tetrahydronaphthalene-1-carboxylic acid and the 2-amino-3-hydroxypyridine used therein, equimolar amounts of 3-methoxy-5,6,7,8-tetrahydronaphthalene-1-carboxylic acid and 2-amino-6-ethyl-3-hydroxypyridine, respectively, there is produced 5-ethyl-2-(3-methoxy-5,6,7,8-tetrahydronaphth-1-yl)oxazolo[4,5-b]pyridine.

Example 7

2-(4-Propoxy-5,6,7,8-tetrahydronaphth-2-yl)oxazolo[4,5-b]pyridine

Step A: Preparation of 4-hydroxy-5,6,7,8-tetrahydronaphthalene-2-carboxylic acid Employing the procedure of Example 6, Step A, but substituting for the 3-amino-5,6,7,8-tetrahydronaphthalene-1-carboxylic acid used therein, an equimolar amount of 4-amino-5,6,7,8-tetrahydronaphthalene-2-carboxylic acid, there is produced 4-hydroxy-5,6,7,8-tetrahydronaphthalene-2-carboxylic acid.

Step B: Preparation of 4-methoxy-5,6,7,8-tetrahydronaphthalene-2-carboxylic acid Employing the procedure of Example 6, Step B, but substituting for the 3-hydroxy-5,6,7,8-tetrahydronaphthalene-1-carboxylic acid used therein, an equimolar amount of 4-hydroxy-5,6,7,8-tetrahydronaphthalene-2-carboxylic acid, there is produced 4-methoxy-5,6,7,8-tetrahydronaphthalene-2-carboxylic acid.

Step C: Preparation of 2-(4-methoxy-5,6,7,8-tetrahydronaphth-2-yl)oxazolo[4,5-b]pyridine Employing the procedure of Example 1, but substituting for the 5,6,7,8-tetrahydronaphthalene-1-carboxylic acid used therein, an equimolar amount of 4-methoxy-5,6,7,8-tetrahydronaphthalene-2-carboxylic acid, there is produced 2-(4-methoxy-5,6,7,8-tetrahydronaphth-2-yl)oxazolo[4,5-b]pyridine.

Step D: Preparation of 2-(4-hydroxy-5,6,7,8-tetrahydronaphth-2-yl)oxazolo[4,5-b]pyridine The product from Step C (5.0 g.) is dissolved in 500 ml. of benzene, 50 g. of aluminum chloride is added quickly portionwise, and the mixture is refluxed for 3 hours. After cooling, the benzene is decanted from an insoluble gum. Ice is added cautiously to the gum to decompose excess aluminum chloride, and 100 ml. of benzene is added and the mixture is stirred for 3 hours. The precipitate is collected, washed with water, and dried to give 2-(4-hydroxy-5,6,7,8-tetrahydronaphth-2-yl)oxazolo[4,5-b]pyridine.

Step E: Preparation of 2-(4-propoxy-5,6,7,8-tetrahydronaphth-2-yl)oxazolo[4,5-b]pyridine A solution of 5.0 mmoles of product from Step D in 5 ml. of dimethylformamide is treated with 5.0 mmoles of sodium hydride/mineral oil emulsion. After stirring 10 minutes 1.0 g. of propyl iodide is added. After stirring 2 hours, the mixture is concentrated in vacuo to remove the dimethylformamide. Water (10 ml.) is added to the residue and the solids are collected and recrystallized from cyclohexane to give 2-(4-propoxy-5,6,7,8-tetrahydronaphth-2-yl)oxazolo[4,5-b]pyridine.

EXAMPLE 8

2-(6-t-Butylindan-4-yl)oxazolo[4,5-b]pyridine

A mixture of 6.0 g. of polyphosphoric acid, 0.5 g. of 6-t-butylindane-4-carboxylic acid and 6.25 g. of 2-amino-3-hydroxypyridine under nitrogen was placed in an oil bath at 150° C. After stirring about 15 minutes at this temperature, the melt was poured into 100 ml. of ice water. The precipitate was collected on a filter and stirred in 25 ml. of 2.5 N sodium hydroxide solution for 10 minutes. The insoluble material was collected on a filter, washed with water and air dried to give 300 mg. of crude product. This was dissolved in 50 ml. of cyclohexane, charcoaled, filtered, concentrated to about 20 ml. and cooled to crystallize 100 mg. of 2-(6-t-butylindan-4-yl)oxazolo[4,5-b]pyridine, m.p. 198°–200° C.

What is claimed is:

1. A compound of structural formula:

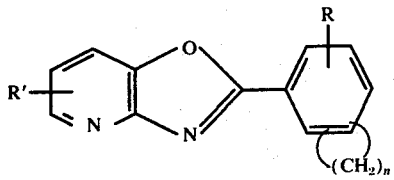

wherein
R is
1. hydrogen,
2. halo,
3. lower alkyl, or
4. lower alkoxy;
R' is
1. hydrogen, or
2. lower alkyl;
n is 3, 4, or 5; and
—(CH$_2$)$_n$ is linked to adjacent carbon atoms of the benzo group.

2. The compound of claim 1 of formula:

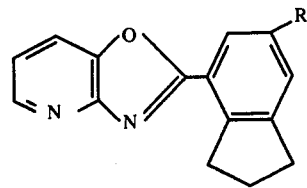

wherein R is lower alkyl.

3. The compound of claim 1 which is 2-(6-t-butylindan-4-yl)oxazolo[4,5-b]pyridine.

4. A method of treating dermatoses which comprises topical administration to a patient in need of such treatment an effective amount of a compound of formula:

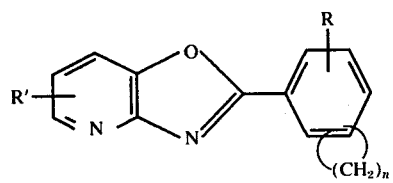

wherein
R is
1. hydrogen,
2. halo,
3. lower alkyl, or
4. lower alkoxy;
R' is
1. hydrogen, or
2. lower alkyl;
n is 3, 4, or 5; and
—(CH$_2$)$_n$ is linked to adjacent carbon atoms of the benzo group.

5. A pharmaceutical composition for topical administration in the treatment of dermatoses comprising a carrier and an effective amount of a compound of formula:

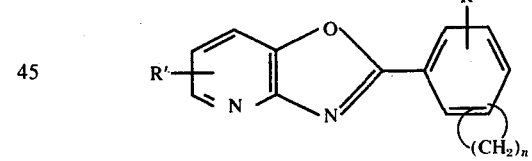

wherein
R is
1. hydrogen,
2. halo,
3. lower alkyl, or
4. lower alkoxy;
R' is
1. hydrogen, or
2. lower alkyl;
n is 3, 4, or 5; and
—(CH$_2$)$_n$ is linked to adjacent carbon atoms of the benzo group.

* * * * *